United States Patent
Lee et al.

(10) Patent No.: US 8,449,478 B2
(45) Date of Patent: May 28, 2013

(54) BIOPSY DEVICE

(75) Inventors: Michael J. Lee, Santa Rosa, CA (US);
William Krimsky, Bel Air, MD (US);
Brad A. Snow, Atlanta, GA (US)

(73) Assignee: Conquest Medical Technologies, Santa Rosa, CA (US)

(*) Notice: Subject to any disclaimer, the term of this patent is extended or adjusted under 35 U.S.C. 154(b) by 1286 days.

(21) Appl. No.: 12/122,229

(22) Filed: May 16, 2008

(65) Prior Publication Data
US 2009/0287114 A1    Nov. 19, 2009

(51) Int. Cl.
*A61B 10/00* (2006.01)
(52) U.S. Cl.
USPC ........................................... 600/567
(58) Field of Classification Search
USPC ........................................... 600/567
See application file for complete search history.

(56) References Cited

U.S. PATENT DOCUMENTS

| | | | |
|---|---|---|---|
| 4,781,202 A | 11/1988 | Janese | |
| 4,785,826 A | 11/1988 | Ward | |
| 4,926,877 A | 5/1990 | Bookwalter | |
| 5,074,311 A | 12/1991 | Hasson | |
| 5,133,360 A | 7/1992 | Spears | |
| 5,183,052 A | 2/1993 | Terwilliger | |
| 5,267,572 A | 12/1993 | Bucalo | |
| 5,823,971 A | 10/1998 | Robinson et al. | |
| 5,848,978 A * | 12/1998 | Cecchi | 600/567 |
| 6,007,495 A | 12/1999 | Matula | |
| 6,007,544 A | 12/1999 | Kim | |
| 6,068,603 A | 5/2000 | Suzuki et al. | |
| 6,083,237 A | 7/2000 | Huitema et al. | |
| 6,110,127 A | 8/2000 | Suzuki et al. | |
| 6,139,508 A * | 10/2000 | Simpson et al. | 600/564 |
| 6,213,957 B1 | 4/2001 | Milliman et al. | |
| 6,315,737 B1 | 11/2001 | Skinner et al. | |
| 6,755,793 B2 | 6/2004 | Lamoureux et al. | |
| 6,792,305 B2 | 9/2004 | Rastorgoueff et al. | |
| 6,875,183 B2 * | 4/2005 | Cervi | 600/567 |
| 7,001,342 B2 | 2/2006 | Faciszewski | |
| 7,033,324 B2 | 4/2006 | Giusti et al. | |
| 7,137,956 B2 | 11/2006 | Nishtalas et al. | |
| 7,229,439 B2 | 6/2007 | Burbank et al. | |
| 7,278,970 B2 | 10/2007 | Goldenberg | |
| 7,311,673 B2 | 12/2007 | Mueller, Jr. et al. | |

* cited by examiner

*Primary Examiner* — Max Hindenburg
*Assistant Examiner* — Renee Danega

(57) ABSTRACT

Aspects of the present invention are generally directed to a biopsy device configured to engage target tissue within a patient and to remove a sample of the target tissue from the patient. The biopsy device comprises an elongate catheter configured to be inserted into a patient. A coring component is disposed at the distal end of the catheter to sample the target tissue.

37 Claims, 14 Drawing Sheets

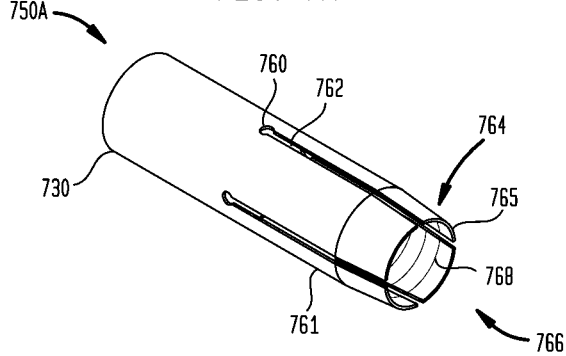
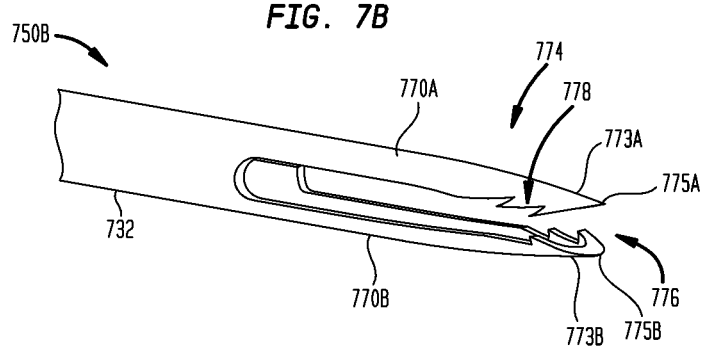
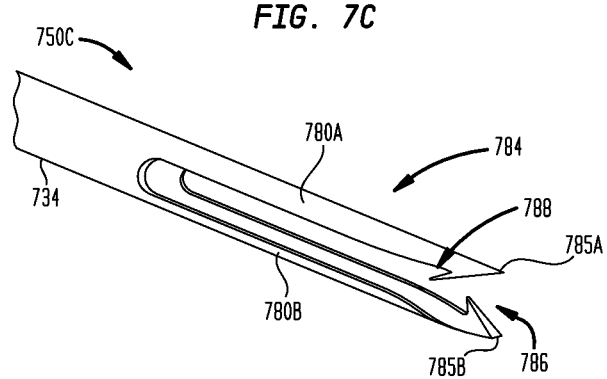

BIOPSY DEVICE

BACKGROUND

1. Field of the Invention

The present invention relates generally to a tissue-sampling device, and more particularly, to a biopsy device.

2. Related Art

For various medical reasons, such as diagnostic tests and the like, it is often necessary for a physician, surgeon or other medical practitioner (generally referred to hereinafter as a "surgeon") to obtain a sample of a patient's body. During these sampling or biopsy procedures, the samples may be taken from a variety of organs and other soft tissue, or from a more rigid structure such as a bone or bone marrow.

There are a variety of medical procedures to obtain a tissue sample. For example, an endoscopic procedure commonly referred to as an endoscopic biopsy procedure, is often used to obtain tissue samples within a patient's body. During an endoscopic biopsy procedure, a sample of a target tissue is removed from a patient with an endoscopic biopsy device having a tissue acquisition element. The endoscopic biopsy device may include an elongate tube having a lighted camera on a distal end, collectively referred to as an endoscope or endoscope camera, that is used by the surgeon to view the target tissue during the biopsy procedure. Other devices or systems for visualizing the sampling procedure may also be used. For example, any radiographic, fluoroscopic, or other navigational or guidance modality, including COT, may also be used for visualizing the sampling procedure.

In certain devices, the biopsy or tissue acquisition element may be passed through a catheter that is separate from the tube having a camera thereon. Likewise, other devices may also be inserted through or around the endoscope.

A sample of the target tissue is generally taken using a brush or a needle attached to a cable within the endoscopic device. Following sampling of the target tissue, the tissue sample is removed from the patient and examined. The tissue is generally examined under a microscope by a pathologist or chemically analyzed using, for example, gas chromatography techniques.

Depending on the target tissue and other physical conditions or circumstances, sampling of internal tissue may be difficult or may require skill to quickly and efficiently obtain an adequate tissue sample to permit proper examination by a pathologist or other medical practitioner.

SUMMARY

In one aspect of the present invention, a device for sampling target tissue within a patient is provided. The device comprises: a coring component having: a longitudinal lumen terminating in a distal opening; and a distal region formed of one or more distally extending blades each having a distal end positioned around the distal opening, wherein the one or more blades are configured to penetrate the target tissue such that a tissue sample having a cross-section defined by the distal ends of the one or more blades is received within the lumen of the coring component via the distal opening, and wherein the blades are configured to substantially sever the tissue sample from the target tissue.

In another aspect of the present invention, a coring component configured to sample a target tissue within a patient is provided. The coring component comprises: a longitudinal lumen terminating in a distal opening; and a distal region formed of one or more distally extending blades each having a distal end positioned around the distal opening, wherein the one or more blades are configured to penetrate the target tissue such that a tissue sample having a cross-section defined by the distal ends of the one or more blades is received within the lumen of the coring component via the distal opening, and wherein the blades are configured to substantially sever the tissue sample from the target tissue.

In another aspect of the present invention a method for obtaining a tissue sample from a target tissue in a patient with a coring component having a longitudinal lumen terminating in a distal opening, a distal region formed of one or more distally extending blades each having a distal end positioned around the distal opening is provided. The method comprises: positioning the coring component such that the distal ends of the blades are adjacent the target tissue; penetrating the target tissue with the blades such that a tissue sample having a cross-section defined by the distal ends of the one or more blades is received within the lumen of the coring component via the distal opening, and substantially severing the tissue sample from the target tissue.

BRIEF DESCRIPTION OF THE DRAWINGS

Illustrative embodiments of the present invention are described herein with reference to the accompanying drawings, in which:

FIG. 7A is a front perspective view of a coring component in accordance with one embodiment of the present invention;

FIG. 7B is a perspective view of a coring component in accordance with one embodiment of the present invention;

FIG. 7C is a perspective view of a coring component in accordance with one embodiment of the present invention;

DETAILED DESCRIPTION

Aspects of the present invention are generally directed to a biopsy device having a coring component configured to engage target tissue of a patient and to remove a sample of the target tissue from the patient. The coring component comprises a longitudinal lumen terminating in a distal opening. A distal region of the coring component is formed of one or more distally extending blades each having a distal end positioned around the distal opening of the lumen. The blades are configured to penetrate the target tissue such that a tissue sample having a cross-section defined by the distal ends of the one or more blades is received within the lumen of the coring component via the distal opening. The blades are configured to substantially sever the tissue sample from the remainder of the target tissue.

In certain embodiments, the coring component comprises two or more elongate blades each having distal ends positioned around the distal opening. In some embodiments, to sever the tissue, one or more of the blades flex inwardly towards a longitudinal axis of the coring component. In the same or other embodiments, the coring component is rotatable relative to the target tissue to facilitate the severing of the tissue sample. In particular embodiments of the present invention, the biopsy device comprises an anchoring element which secures the device to the target tissue. In certain embodiments, the biopsy device may further include a tissue retention feature which secures the tissue sample in the lumen of the coring component.

Figure 1:
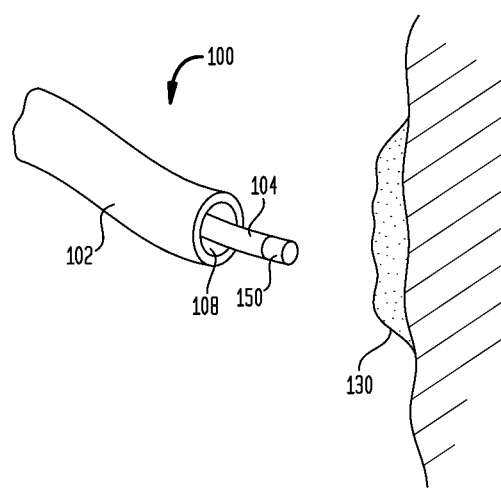
FIG. 1 is a perspective view of a distal end of an exemplary biopsy device in accordance with embodiments of the present invention.

FIG. 1 is a perspective view of a distal region of an exemplary biopsy device 100 that may be used to sample a target tissue within a patient in accordance with embodiments of the present invention. Although the present invention will be discussed herein with reference to specific types of biopsy devices and procedures, namely endoscopic biopsy devices and procedures, it should be appreciated that embodiments of the present invention may be used in conjunction with any other biopsy or tissue sampling device/procedure.

In certain optional embodiments of the present invention, biopsy device 100 comprises a tube or sheath 102 which is introduced into the patient to facilitate the positioning of sampling component 150 adjacent target tissue 130. The target tissue comprises a tissue which the surgeon desires to obtain a sample thereof. In accordance with embodiments of the present invention, the target tissue may be a portion of a tissue, bone or organ surface, a portion of the tissue, bone or organ lying beneath the surface, or any other portion of a tissue, organ or bone.

In embodiments in which sheath 102 is provided, catheter 104 may be introduced into a lumen 108 of sheath 102. As would be appreciated, catheter 104 may be introduced into lumen 108 during a biopsy procedure or catheter 104 may be preoperatively positioned within lumen 108. Regardless whether catheter 104 is introduced into lumen 108 prior to or during a biopsy procedure, it should be appreciated that catheter 104 is movable within sheath 102 and may be extended from a distal end of the sheath.

FIG. 1 illustrates an embodiment of biopsy device 100 in which catheter 104 extends from the distal end of sheath 102. In the illustrated embodiment, a sampling component 150 is integrated at the distal end of catheter 104. Sampling component 150 is configured to obtain a sample of a patient's target tissue 130.

Figure 2A:
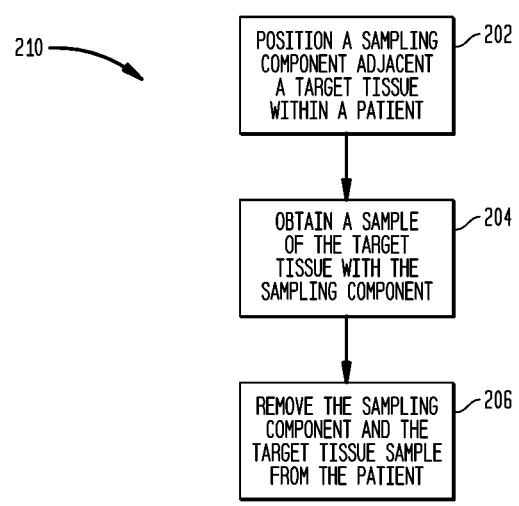
FIG. 2A is a high-level flowchart illustrating an exemplary sampling procedure in accordance with embodiments of the present invention.

FIG. 2A is a high-level flowchart illustrating a surgical procedure 210 for obtaining a tissue sample from a patient with an endoscopic biopsy device, in accordance with embodiments of the present invention. At block 202, a sampling component is positioned adjacent a target tissue within the patient. Embodiments of a biopsy device having components to position a sampling component adjacent the target tissue are described below with reference to FIGS. 4A-4C.

At block 204, the sampling component is used to obtain a tissue sample from the target tissue. Obtaining a tissue sample is described in more detail below with reference to FIG. 2B. At block 206, after a tissue sample is obtained, the sampling component and the tissue sample are removed from the patient.

Figure 2B:
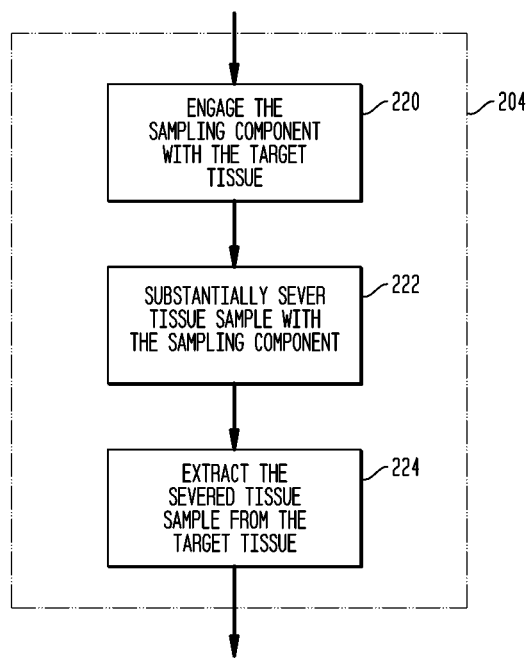
FIG. 2B is a mid-level flowchart illustrating the obtaining a sample of a target tissue in accordance with embodiments of block 204 of FIG. 2A.
Figure 3A:
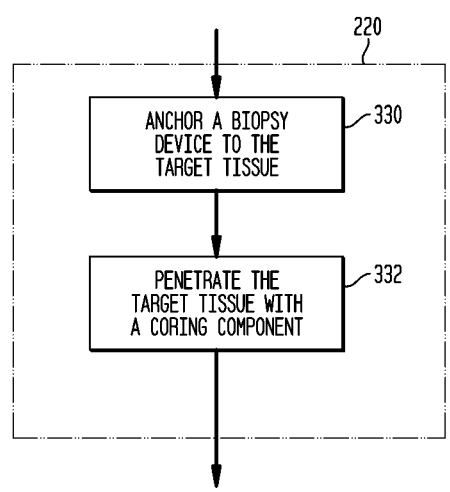
FIG. 3A is a detailed flowchart illustrating the engagement of a sampling component with a target tissue in accordance with one particular embodiment of block 220 of FIG. 2B.
Figure 3B:
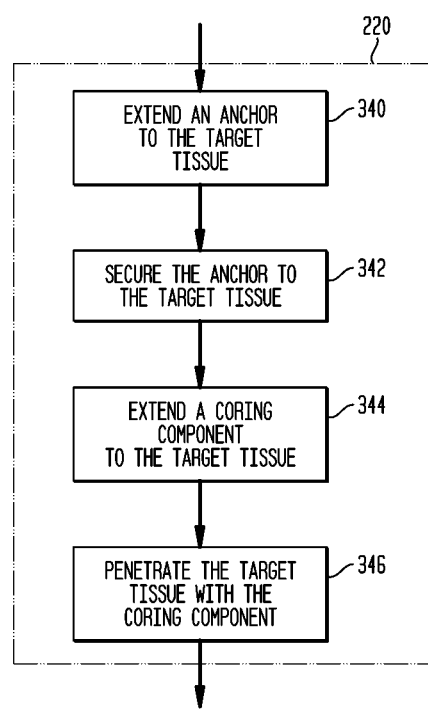
FIG. 3B is a detailed flowchart illustrating the engagement of a sampling component with a target tissue in accordance with one particular embodiment of block 220 of FIG. 2B.

FIG. 2B is a mid-level flowchart illustrating the operations performed to obtain a tissue sample in accordance with embodiments of block 204 of FIG. 2A. At block 220, the sampling component engages the target tissue. FIGS. 3A and 3B illustrate various embodiments for engaging the target tissue with the sampling component.

At block 222, the sampling component substantially severs a portion of the tissue sample from the remainder if the target tissue. Substantial severing of the tissue sample from the target tissue is described below with reference to FIGS. 7A-8B. At block 224, the severed tissue sample is extracted from the target tissue.

FIG. 3A is a flowchart illustrating particular embodiments of block 220 of FIG. 2B in which a sampling component of a biopsy device engages the target tissue. In this embodiment, the sampling component comprises a coring component configured to penetrate a target tissue and to extract a tissue sample from the target tissue. At block 330 the biopsy device is anchored or secured to the target tissue by, for example, an anchoring element. The device may be secured to the target tissue to ensure that a desired portion of the target tissue is sampled by the coring component.

Following anchoring of the biopsy device to the target tissue, at block 332 the coring component penetrates the target tissue. As detailed further below, a surgeon may operate the biopsy device so as to cause the distal end of the coring component to penetrate the target tissue.

FIG. 3B is a flowchart illustrating certain other embodiments of block 220 of FIG. 2B in which a coring component is engaged with the target tissue. In the embodiments illustrated in FIG. 3B, the biopsy device includes an anchoring element in the form of an extendible anchor. As described in more detail below, in alternative embodiments the anchoring element may be attached to, or comprise part of the coring component. In certain embodiments, the anchoring element may comprise the coring component itself that is extended out a controlled distance. As shown, at block 340 the anchor may be extended from the biopsy device to the target tissue. In accordance with embodiments discussed below, at block 342 at least a portion of the anchor is secured or affixed to the target tissue.

After the anchor is secured to the target tissue, the coring component is extended to target tissue at block 344. At block 346, the coring component penetrates the target tissue such that a portion of the target tissue having a cross-section defined by the distal end of the coring component is received within the coring component.

Figure 4A:
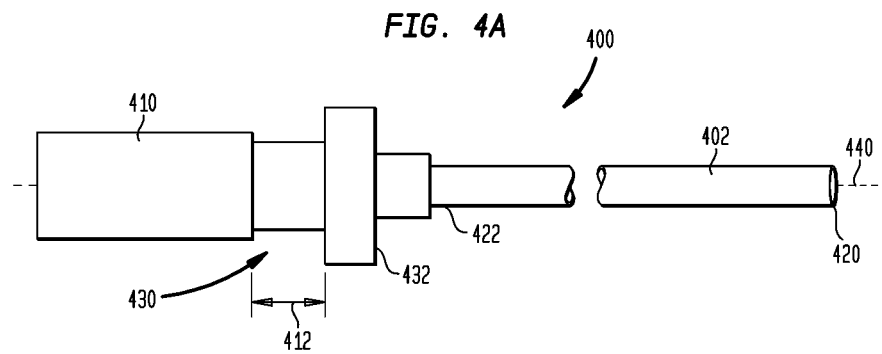
FIG. 4A is a simplified side view of one embodiment of components of a biopsy device which may be used by a surgeon to position a sampling component at a desired location within a patient.
Figure 4B:
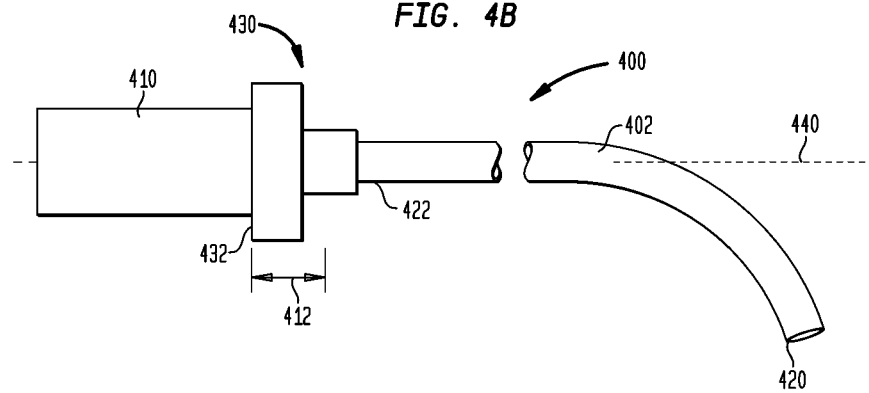
FIG. 4B is a simplified side view of the embodiment of components of a biopsy device shown in FIG. 4A in which the distal region of the device is shown in a curved configuration.
Figure 4C:
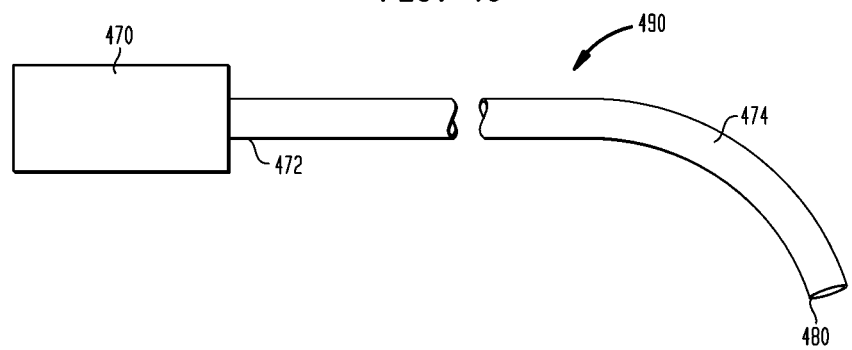
FIG. 4C is a simplified side view of one embodiment of components of a biopsy device which may be used by a surgeon to position a sampling component at a desired location within a patient.

As noted above with reference to block 202 of FIG. 2A, a distal end of the sampling component is positioned adjacent the target tissue prior to obtaining a sample of the target tissue. A biopsy device in accordance with embodiments of the present invention may include a variety of mechanisms or elements which permit a surgeon to guide the distal end of the sampling component to a desired location adjacent the target tissue. FIGS. 4A-4C illustrates particular optional embodiments of a biopsy device 400 in which a sheath 402 is used to guide the sampling component to a desired location.

In the embodiments of FIGS. 4A and 4B, biopsy device 400 includes a sheath 402 having a proximal end 422 and a distal end 420, an endoscope body 410, and articulation elements 430. As would be appreciated, endoscope body 410 may include a variety of functional components.

In the embodiment of FIGS. 4A and 4B, articulation elements 430 provide a surgeon with the ability to guide a sampling component (not shown) such that a distal end of the sampling component is adjacent the target tissue. Articulation elements 430 comprise an articulation control section 432 and one or more wires (not shown). In the illustrated embodiment, articulation control section 432 is positioned between body 410 and proximal end 422 of sheath 402. The one or more wires extend from control section 432 through sheath 402 to distal end 420 of sheath 402.

In the illustrated embodiments of the present invention, actuation of control section 432 exerts a push or pull force on one or more of the wires extending between control section 432 and distal end 420 of sheath 402. The push or pull forces on the wires cause distal end 420 of sheath 420 to deflect at one or more angles.

For example, as shown in FIG. 4A, control section 432 is positioned in a first configuration and distal end of sheath 402 is substantially aligned with a longitudinal axis 440 of body 410. As shown in FIG. 4B, control section 432 is actuated by movement a distance 412 along axis 440 in the direction of body 410. Actuation of control section 432 causes distal end 420 to deflect a distance from longitudinal axis 440. In these embodiments, the magnitude of the deflection of distal end 420 may be controlled by moving control section 432 less than distance 412.

As noted, in the embodiments illustrated in FIGS. 4A and 4B, control section 432 is configured to slide along axis 440 to exert push or pull forces on the wires extending to distal end 420. However, it should be appreciated that control section 432 may be actuated in a variety of manners. For example, in certain embodiments control section 432 may comprise a knob configured to be rotated in or more directions. In these embodiments, the magnitude of the deflection of distal end 420 is controlled by the rotation of the knob by the surgeon. In still other embodiments, control section 432 comprises a dual deflection control. As would be appreciated by one of ordinary skill in the art, any conventional mechanism that uses a push/pull, twist, rotation or other similar motion to actuate, deflect and/or steer distal end 420 may be used in accordance with embodiments of the present invention.

In other embodiments of FIGS. 4A and 4B, magnetic fields may be used to control the deflection of distal end 420. More specifically, internal magnets incorporated into biopsy device 400, or external magnets may be used to control the deflection of distal end 420.

In additional embodiments, shape memory materials may be used to cause a deflection of distal end 420. In these embodiments, upon the occurrence of a predetermined condition, the shape memory material causes distal end 420 to adopt a desired configuration. For example, in certain embodiments, shape memory wires may be included in sheath 402.

FIG. 4C illustrates alternative embodiments of the present invention in which articulation elements 432 have been omitted. In the illustrated embodiment, biopsy device 490 includes a sheath 474 having a proximal end 472 and a distal end 480 and an endoscope body 470. As would be appreciated, endoscope body 470 may include a variety of functional components. In certain embodiments illustrated in FIG. 4C, the magnitude of the deflection of distal end 480 may be controlled by, for example, a surgeon prior to insertion of sheath 474 into the patient. In these embodiments, the surgeon may manually set the magnitude of deflection of distal end 480. In these embodiments, at least a distal region of sheath 474 comprises a material that is flexible enough to be manually curved by the surgeon to a desired angle, but which has sufficient strength to maintain the desired angle during the biopsy procedure.

In further embodiments, the distal region of sheath 474 may comprise a shape memory material. In these embodiments, distal end 480 has a first configuration prior to insertion into a patient. Following insertion of sheath 474, distal end 480 adopts a second configuration. As would be appreciated by one of ordinary skill in the art, distal end 480 may adopt the second configuration in response to, for example, a change in temperature or application of an electrical current thereto.

In still other embodiments illustrated in FIG. 4C, the deflection of distal end 420 is fixed prior to insertion during, for example, manufacture of sheath 474. In such embodiments, a distal region of the sheath has a fixed radius of curvature.

Furthermore, although FIGS. 4A-4C have been described with reference to deflection of a distal end 420, 480, it should be appreciated that any other methods now know or later developed for guiding or steering a sampling component to a location adjacent the target tissue are also within the scope of the present invention. It should also be appreciated that use of a sheath in embodiments of the present invention is optional and not required. For example, in certain embodiments a guide wire may be introduced into the patient and used by a surgeon to guide the sampling component to a location adjacent the target tissue.

Figure 5:
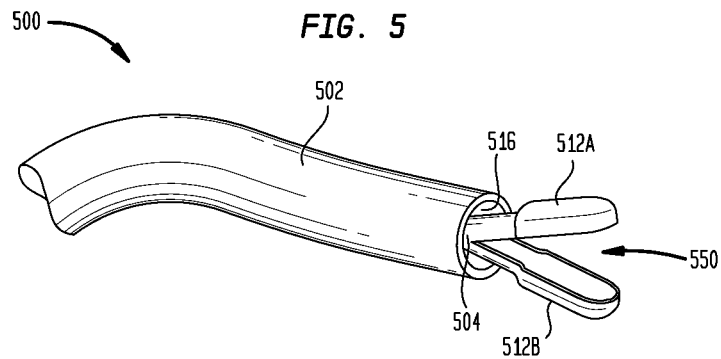
FIG. 5 is a perspective view of a biopsy device having a jaws arrangement for sampling a target tissue within a patient in accordance with embodiments of the present invention.

FIG. 5 is a perspective view of a distal region of a biopsy device 500 in accordance with particular embodiments of the present invention. As shown in FIG. 5, biopsy device 500 comprises a sheath 502 having a lumen 516 there through. Extending through lumen 516 is an elongate catheter 504 having an integrated sampling component 550 disposed at the distal end thereof configured to obtain a sample of a target tissue.

In the illustrated embodiment, sampling component 550 comprises a jaws arrangement 550. In these embodiments, jaws arrangement 550 comprises a pair of opposing jaws 512 configured to be positioned around a portion of the target tissue, referred to herein as a tissue sample. Following positioning of opposing jaws 512 around the tissue sample, the surgeon may actuate jaws 512 so as to close the jaws about the tissue sample. In certain embodiments, jaws 512 may have sharpened, serrated or other edges such that closure of jaws 512 substantially severs the tissue sample from the remainder of the target tissue. As would be appreciated by one of ordinary skill in the art, biopsy device 500 may include various components which permit a surgeon to open and/or close jaws 512.

Figure 6:
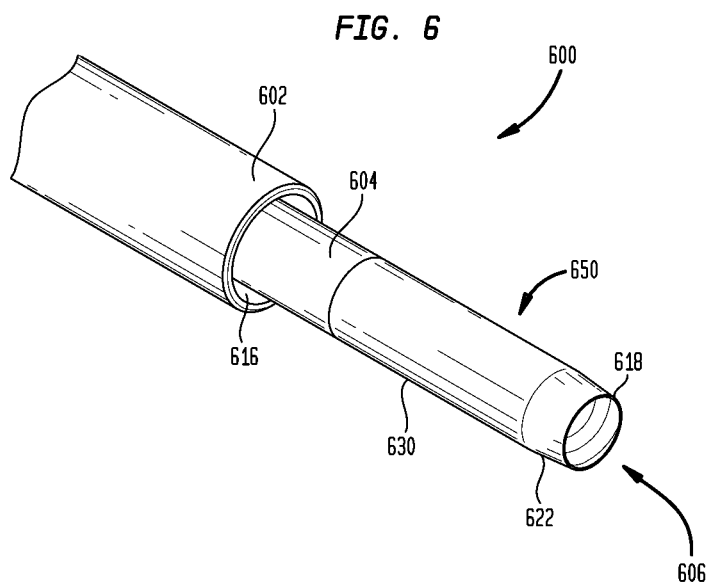
FIG. 6 is a perspective view of a biopsy device having a coring component for sampling a target tissue within a patient in accordance with embodiments of the present invention.

FIG. 6 is a perspective view of a distal region of a biopsy device 600 in accordance with embodiments of the present invention. Biopsy device 600 is configured to engage target tissue within a patient and to remove a sample of the target tissue from the patient.

As shown in FIG. 6, biopsy device 600 comprises a sheath 602 having an elongate catheter 604 extending therethrough. An integrated coring component 650 is disposed at the distal end of catheter 604 to sample a target tissue. Coring component 650 comprises a longitudinal lumen terminating in a distal opening 606. The lumen of coring component 650 is operationally contiguous with the lumen of catheter 604.

A proximal region of coring component 650, shown as shaft 630, is permanently or removably connected to the distal end of catheter 604, and a distal region of the coring component is formed of one or more distally extending blades each having a distal end positioned around distal opening 606. The blades are configured to penetrate the target tissue such that a tissue sample having a cross-section defined by the distal ends of the one or more blades is received within the lumen of coring component 650 via distal opening 606. The blades are configured to substantially sever the tissue sample from the remainder of the target tissue.

In the embodiments illustrated in FIG. 6, the distal region of coring component 650 is formed as a blade arrangement 622. Blade arrangement 622 has one or more cutting edges 618 positioned around distal opening 606 of coring component 650. Blade arrangement 622 penetrates the target tissue such that a portion of the target tissue having a cross-section defined by the distal end of blade arrangement 622 is received within the lumen of coring component 650 via distal opening 606. The portion of the target tissue received within coring component 650 is referred to herein as a tissue sample. As described in more detail below, blade arrangement 622 is configured to substantially sever the tissue sample from the remainder of the target tissue.

As shown in FIG. 6, blade arrangement 622 has a single cutting edge substantially surrounding opening 606. FIGS. 7A through 7C illustrate other embodiments of coring components in accordance with embodiments of the present invention.

As noted above, a surgeon positions coring component 650 at a location such that the distal end of the coring component is adjacent the target tissue. Coring component 650 is extended to the target tissue and engaged therewith. As would be appreciated by one of ordinary skill in the art, biopsy device 600 may include various components which permit a surgeon to extend coring component 650 to the target tissue. For example, in certain embodiments, biopsy device 600 comprises one or more push/pull wires which allow a surgeon to selectively extend coring component 650. Such push/pull wires may be controlled, for example, via by thumb knobs or various other mechanisms.

In other embodiments, biopsy device 600 could include one or more shape memory wires. In such embodiments, the length of the shape memory wires may be controlled so as to selectively extend coring component 650. The length of such shape memory wires may be controlled by, for example, by applying an electrical current to the wires.

In still other embodiments, a syringe/needle mechanism may be included in biopsy device 600 to selectively extend coring component 650. As would be appreciated by one of ordinary skill in the art, the above mechanisms for extending coring component 650 have been provided for illustration purposes only and any other known component or mechanism which permits a surgeon to extend the coring component may also be included in biopsy device 600.

Although FIG. 6 has been discussed with reference to the use of one more components to extend coring component 650 to the target tissue, it should be appreciated that such components are optional and are not required. For example, in certain embodiments, a surgeon may manually exert a force on catheter 604 to cause coring component 650 to be extended to the target tissue.

As noted above, blade arrangement 622 is configured to penetrate the target tissue such that a portion of the target tissue having a cross-section defined the distal end of blade arrangement 622 is received within the lumen of coring component 650 via distal opening 606. In certain embodiments of the present invention, blade arrangement 622 penetrates the target tissue in response to one or both of a longitudinal force exerted on the coring component 650 in the direction of the target tissue or a rotational force exerted on coring component 650. These rotational and/or longitudinal forces on coring component 650 may be applied in a variety of manners. For example, in certain embodiments, a surgeon may manually apply a longitudinal or rotational force. In other embodiments, biopsy device 600 may comprise any known articulation mechanism or element that permits a surgeon to apply the desired longitudinal or rotational force.

Also as noted above, blade arrangement 622 is configured to substantially sever the tissue sample from the remainder of the target tissue so that tissue sample suitable for proper examination is obtained during the sampling procedure. As noted above, certain sampling devices are unable to obtain large enough samples suitable for all types of examination. Blade arrangement 622 may sever the tissue sample in a variety of manners. In the specific embodiment of FIG. 6, blade arrangement 622 substantially severs the portion of target tissue positioned within coring component 650 via, for example, rotation of coring component 650 about a longitudinal axis extending through opening 606. In response to the rotation of coring component 650, the distal end of blade arrangement 622 substantially reduces the cross-section of the portion of the target tissue positioned proximate to opening 606. As described below in more detail with reference to FIG. 7, coring component 650 may be rotated manually by a surgeon or through the use of one or more elements included within biopsy device 600.

As explained above with reference to FIG. 2B, after the tissue sample has been substantially severed from the remainder of the target tissue, the tissue sample may be extracted from the target tissue by removing coring component 650 from the target tissue. Because, in certain embodiments, blade arrangement 622 substantially severs the tissue sample, the tissue sample may remain partially attached to the remainder of the target tissue. As discussed below in more detail, coring component 650 is configured to firmly secure the tissue sample such that removal of coring component 650 causes the tissue sample to become completely detached from the remainder of the target tissue.

In one exemplary embodiment, a surgeon may remove coring component 650 from the target tissue by manually exerting a longitudinal or rotational force on coring component 650. In other embodiments, various components or mechanisms may be included in biopsy device 600 which provide the surgeon with the ability to remove coring component 650 from the target tissue. In particular, any of the components or mechanisms discussed above which permit a surgeon to insert coring component 650 into the target tissue, or which are used to extend coring component 650 to the target tissue, may also be used to remove the coring component from the target tissue.

Following extraction of the tissue sample, biopsy device 600 and the tissue sample may be removed from the patient. In these embodiments, biopsy device 600 may include one or more mechanisms or elements which permit a surgeon to guide the biopsy device from the patient. For example, any of the articulation elements or mechanisms described above with reference to FIGS. 4A-4C may be further used by the surgeon to guide biopsy device 600 from the patient.

As noted, in embodiments of the present invention, a lumen extends through catheter 604 that is operationally contiguous with a lumen of coring component 650. The operational contiguity of the lumens allows a surgeon to use the lumen during the biopsy procedure. For example, in certain embodiments, various devices may be inserted through the contiguous lumens such as optical devices, probes, forceps, needles, brushes, etc. Furthermore, the contiguous lumens permit a surgeon to deliver various treatments there through, before, during or after the obtaining the tissue sample.

FIG. 7A is a front perspective view of a coring component 750A in accordance with particular embodiments of FIG. 6. As shown in FIG. 7A, coring component 750A comprises an elongate element having longitudinal lumen terminating in a distal opening 766. A distal region of coring component 750A is formed of a blade arrangement 764.

As shown in FIG. 7A, blade arrangement 764 comprises an elongate shaft 730 and plurality of distally extending blades 761 having their distal ends positioned around opening 766 of coring component 750A. In some embodiments, the distal ends of blades 761 are radially positioned around opening 766. The distal end of each blade 761 is a cutting edge 765. As shown in FIG. 7A, blade arrangement 764 comprises four blades 761. However, it should be appreciated that blade arrangement 764 may comprise more or less blades 761.

In the illustrated embodiment, each blade 761 has an approximately lunate cross-section. In other embodiments, each blade 761 has a cross-section of other geometries or shapes. Likewise in embodiments of the present, the cross-sections of each blade are not uniform. As shown, the concave portion of each blade is proximate to the lumen of coring component 750A.

As described above with reference to FIG. 6, blade arrangement 764 is configured to penetrate the target tissue such that a portion of the target tissue having a cross-section defined by the distal end of blade arrangement 764 is received within the lumen of coring component 750A via distal opening 766. Also, as noted above, blade arrangement 764 is configured to substantially sever the portion of the target tissue received within coring component 750A, referred to as the tissue sample, from the remainder of the target tissue.

Blade arrangement 764 may substantially sever the tissue sample from the target tissue in a variety of manners. For example, in certain embodiments, coring component 750A is rotatable with respect to the target tissue. In response to the rotation of coring component 750A, cutting edges 765 of blades 761 substantially reduce the cross-sectional diameter of the portion of the target tissue positioned there between proximate to opening 766.

In the same or other embodiments, blade arrangement 764 may substantially sever the tissue sample via closure of blades 761 to obtain a tissue sample suitable for proper examination. As noted above, certain sampling devices are unable to obtain large enough samples suitable for all types of examination.

In the illustrated embodiments, at least one blade 761 is configured to flex inwardly towards a longitudinal axis extending through coring component 750A. The inward flexing of one or more blades 761 causes blades 761 to cut through the target tissue positioned there between so as to substantially sever the tissue sample from the remainder of the target tissue. These embodiments are described below in more detail with reference to FIGS. 8A and 8B.

In certain embodiments of FIG. 7A, each blade 761 is separated from adjacent blades by an elongate slit 762. Elongate slit 762 extends from opening 766 to a substantially circular aperture 760. Aperture 760 may enhance the inward flexing of one or more blades 761 during penetration of blades 761.

In certain embodiments of the present invention, the tissue sample may be substantially severed from the target tissue via a combination of inward flexing of one or more blades 761 and rotation of coring component 750A.

As explained above with reference to FIG. 2B, following substantial severing of the tissue sample, the tissue sample is extracted from the target tissue by removing coring component 750A from the target tissue. As discussed above with reference to FIG. 6, coring component 750A may be removed from the target tissue in a variety of manners. In particular, any of the components or mechanisms discussed above which permit a surgeon to insert or remove coring component 650 may also be used to remove coring component 750A from the target tissue.

As noted above, because blade arrangement 764 substantially severs the tissue sample, the tissue sample may remain partially attached to the remainder of the target tissue. As such, coring component 750A is configured to firmly secure the tissue sample such that the tissue sample is completely detached from the remainder of the target tissue during removal of coring component 750A from the target tissue.

In certain embodiments, blade arrangement 764 may firmly secure the tissue sample so as to permit detachment of the tissue sample from the remainder of the target tissue. In other embodiments, as shown in FIG. 7A, coring component 750A may further include a retention feature 768 to assist in the extraction of the tissue sample. In these embodiments, following penetration of blade arrangement 764 into the target tissue, retention feature 768 secures the tissue sample within the lumen of coring component 750A. During removal of coring component 750A from the target tissue, retention feature 768 remains secured to the tissue sample, thereby exerting an additional force on the tissue sample and further ensuring that the tissue sample is fully detached from the remainder of the target tissue. Tissue retention feature 768 has the further advantage of substantially preventing the tissue sample from being detached from the device during removal of the device from the patient.

In the illustrated embodiment of FIG. 7A, retention feature 768 may comprise a textured surface 768 of at least a portion of blade arrangement 764. More specifically, textured surface 768 may comprise a textured portion of a surface of one or more blades 761 adjacent the lumen of coring component 750A. In these embodiments, textured surface 768 attaches to the tissue sample and assists in securing the tissue sample within coring component 750A.

Various embodiments of retention feature 768 are within the scope of the present invention. For example, in one exemplary embodiment, retention feature 768 may comprise an adhesive applied to at least a portion of blade arrangement 768. In these embodiments, the adhesive has an adhesive force configured to secure tissue sample within coring component 750A, but which may be overcome by a surgeon with sufficient manual force following removal of coring component 750A from the patient. In these embodiments, retention feature 768 may comprise a reusable adhesive, such as a Gecko-Mussel adhesive.

In further embodiments, retention feature 768 may comprise a suction system included in the biopsy device configured to provide suction at or near coring component 750A. For example, in one such embodiment, suction may be provided through the lumen of coring component 750A to exert a force on the tissue sample and to assist in retaining the tissue sample therein. In other embodiments, suction may be provided around coring component 750A. Embodiments in which suction may be provided are described in more detail below with reference to FIGS. 13A-13C.

In other embodiments, retention feature 768 may comprise one or more additional elements at or in coring component 750A. For example, in one such embodiment, retention feature 768 may comprise a needle positioned within coring component 750A to secure the tissue sample within the lumen of coring component 750A. These embodiments are described below in more detail with reference to FIGS. 11A and 11B.

In other such embodiments, retention feature 768 may comprise a pair of opposing jaws. In these embodiments, opposing jaws are positioned within coring component 750A and are configured to secure the tissue sample within coring component 750A by attaching to at least a portion of the tissue sample. These embodiments are described below in more detail with reference to FIGS. 10A and 10B.

In still other embodiments, retention feature 768 may comprise one or more barbs or spikes provided on blade arrangement 764. These embodiments are described below with reference to FIGS. 7B and 7C.

Furthermore, as noted above, each blade 761 includes cutting edges 765 disposed at the distal end there of blades 761. It should be appreciated that each blade 761 may also include additional cutting edges. For example, each blade may include one or more longitudinally extending cutting edges.

FIG. 7B is a perspective view of a coring component 750B in accordance with certain embodiments of FIG. 6. As shown in FIG. 7B, coring component 750B comprises an elongate element having a longitudinal lumen terminating in a distal opening 776. A distal region of coring component 732 is formed of a blade arrangement 764.

As shown in FIG. 7B, blade arrangement 774 comprises a plurality of distally extending blades 770 having their distal ends positioned around distal opening 776 of coring component 750B. The distal end of each blade 770 is a cutting edge 775. As shown in FIG. 7B, blade arrangement 774 comprises a pair of opposing blades 770. In some embodiments, the distal ends of blades 761 are radially positioned around opening 776. However, it should be appreciated that blade arrangement 770 may comprise more or less blades 770.

In the illustrated embodiment, each blade 770 has an approximately lunate cross-section. In other embodiments, each blade 770 has a cross-section of other geometries or shapes. Likewise in embodiments of the present, the cross-sections of each blade are not uniform. As shown, the concave portion of each blade is proximate to the lumen of coring component 750B.

Also, in particular embodiments illustrated in FIG. 7B, the distal region of each blade 770 adjoining cutting edges 775 comprises a non-planar surface. For example, as described in more detail with reference to FIG. 8A, the distal region of blades 770 may comprise a curved or beveled surface 773 (generally and collectively referred to herein as a "beveled surface").

As described above with reference to FIGS. 6 and 7A, blade arrangement 774 is configured to penetrate the target tissue such that a portion of the target tissue having a cross-section defined by the distal end of blade arrangement 774 is received within the lumen of coring component 750B via distal opening 766. Also, as noted above, blade arrangement 774 is configured to substantially sever the portion of the target tissue received within coring component 750B, referred to as the tissue sample, from the remainder of the target tissue.

Blade arrangement 774 may substantially sever the tissue sample from the target tissue in a variety of manners. For example, in certain embodiments, coring component 750B is configured to be rotatable with respect to the target tissue. In response to the rotation of coring component 750B, cutting edges 775 of blades 770 substantially reduce the cross-sectional diameter of the portion of the target tissue positioned there between proximate to distal opening 776.

In the same or other embodiments, blade arrangement 774 may substantially sever the tissue sample via closure of blades 770. In these embodiments, at least one blade 770 is configured to flex inwardly towards a longitudinal of coring component 750B. In specific embodiments, the at least one blade flexes inwards towards a longitudinal axis through a geometric center of opening 776. The inward flexing of one or more blades 770 causes blades 770 to cut through the target tissue positioned there between so as to substantially sever the tissue sample from the remainder of the target tissue. These embodiments are described below in more detail with reference to FIGS. 8A and 8B.

In certain embodiments of the present invention, the tissue sample may be substantially severed from the target tissue via a combination of inward flexing of one or more blades 770 and rotation of coring component 750B.

As described above with reference to FIG. 2B, following substantial severing of the tissue sample, the tissue sample is extracted from the target tissue by removing coring component 750B from the target tissue. As described above with reference to FIG. 7A, coring component 750B may be removed from the target tissue in a variety of manners.

Because blade arrangement 774 substantially severs the tissue sample, the tissue sample may remain partially attached to the remainder of the target tissue. As such, coring component 750B is configured to firmly secure the tissue sample so that the tissue sample is completely detached from the remainder of the target tissue during removal of coring component 750B.

In other embodiments, coring component 750B may further include a retention feature 778 to assist in the extraction of the tissue sample. In these embodiments, following penetration of blade arrangement 774 into the target tissue, retention feature 778 secures the tissue sample within the lumen of coring component 750B. During removal of coring component 750B from the target tissue, retention feature 778 remains secured to the tissue sample thereby exerting an additional force on the tissue sample and further ensuring that the tissue sample is fully detached from the remainder of the target tissue.

As shown in FIG. 7B, retention feature 778 comprises a plurality of barbs 778 positioned on the surface of blades 770 adjacent the lumen of coring component 750B. In these embodiments, following penetration of blades 770 into the target tissue, barbs 778 attach to the tissue sample. When the surgeon removes coring component 750B from the target tissue, barbs 778 exert a force on the tissue sample to retain the tissue sample within coring component 750B.

In the specific embodiment illustrated in FIG. 7B, barbs 778 are positioned on blades 770 such that the point of each barb at least partially faces away from opening 776. As such, when barbs 778 adhere to the tissue sample, barbs 778 exert a force on the tissue sample in a direction substantially opposite the remainder of the target tissue.

Although FIG. 7B has been described with reference to barbs 778, it should be appreciated that other retention features may also be used with coring component 750B. For example, as described above with reference to FIG. 7A, coring component 750B may further include a textured surface, an adhesive applied to at least a portion of blade arrangement 774, a needle or a set of opposing jaws positioned within coring component, spikes, etc. In other embodiments, suction may be provided by the biopsy device to retain the tissue sample in coring component 750B.

In the illustrated embodiments, each blade 770 includes cutting edges 775 disposed at the distal end there of blades 770. It should be appreciated that each blade 770 may also include additional cutting edges. For example, each blade may include one or more longitudinally extending cutting edges.

FIG. 7C is a perspective view of a coring component 750C in accordance with certain embodiments of FIG. 6. As shown in FIG. 7C, coring component 750C comprises an elongate element having a longitudinal lumen terminating in a distal opening 786. A distal region of coring component 750C is formed of a blade arrangement 784.

As shown in FIG. 7C, blade arrangement 784 comprises a plurality of distally extending blades 780 having their distal ends positioned around distal opening 786 of coring component 750C. The distal end of each blade 761 is a cutting edge 785. In some embodiments, the distal ends of blades 761 are radially positioned around opening 786. As shown in FIG. 7C, blade arrangement 784 comprises a pair of opposing blades 780. However, it should be appreciated that blade arrangement 780 may comprise more or less blades 780.

In the illustrated embodiment, each blade 780 has an approximately lunate cross-section. In other embodiments, each blade has a cross-section of other geometries or shapes. Likewise in embodiments of the present, the cross-sections of each blade are not uniform. As shown, the concave portion of each blade is proximate to the lumen of coring component 750C.

As described above with reference to FIGS. 6-7B, blade arrangement 784 is configured to penetrate the target tissue such that a portion of the target tissue having a cross-section defined by the distal end of blade arrangement 784 is received within the lumen of coring component 750C via distal opening 786. Also, as noted above, blade arrangement 784 is configured to substantially sever the portion of the target tissue received within coring component 750C, referred to as the tissue sample, from the remainder of the target tissue.

Blade arrangement 784 may substantially sever the tissue sample in a variety of manners. For example, as noted above, in certain embodiments, coring component 750C is rotatable with respect to the target tissue. In response to the rotation of coring component 750C, cutting edges 785 of blades 780 substantially reduce the cross-sectional diameter of the portion of the target tissue positioned there between proximate to opening 776.

In the same or other embodiments, blade arrangement 784 may substantially sever the tissue sample via closure of blades 780. In these embodiments, at least one blade 780 is configured to flex inwardly towards a longitudinal axis of coring component 750C. In specific embodiments, one or more blades flex inwardly towards an axis extending through the geometric center of opening 786. The inward flexing of one or more blades 780 causes blades 780 to cut through the target tissue positioned there between so as to substantially sever the tissue sample from the remainder of the target tissue. These embodiments are described below in more detail with reference to FIGS. 8A and 8B.

In certain embodiments of the present invention, the tissue sample may be substantially severed from the target tissue via a combination of inward flexing of one or more blades 780 and rotation of coring component 750C.

As explained above with reference to FIG. 2B, following substantial severing of the tissue sample, the tissue sample may be extracted from the target tissue by removing coring component 750C from the target tissue. As described above with reference to FIG. 7A, coring component 750C may be removed from the target tissue in a variety of manners.

As noted above, because blade arrangement 784 substantially severs the tissue sample, the tissue sample may remain partially attached to the remainder of the target tissue. As such, coring component 750C is configured to firmly secure the tissue sample such that the tissue sample is completely detached from the remainder of the target tissue during removal of coring component 750C.

In other embodiments, coring component 750C may further include a tissue retention feature 788 to assist in the extraction of the tissue sample from the target tissue. In these embodiments, following penetration of blade arrangement 784 into the target tissue, retention feature 788 secures the tissue sample within the lumen of coring component 750C. During removal of coring component 750C from the target tissue, retention feature 788 remains secured to the tissue sample, thereby exerting an additional force on the tissue sample and further ensuring that the tissue sample is fully detached from the remainder of the target tissue.

As shown in FIG. 7C, retention feature 788 comprises opposing barbs 788, each positioned on the surface of blades 780 adjacent opening 786. In these embodiments, following penetration of blades 780 into the target tissue, barbs 788 attach to the tissue sample. When the surgeon removes coring component 750C from the target tissue, barbs 788 exert a force on the tissue sample to retain the tissue sample within the lumen of coring component 750C.

In the specific embodiment illustrated in FIG. 7C, barbs 788 are positioned on blades 780 such that the point of each barb at least partially faces away from opening 786. As such, when barbs 788 attach to the tissue sample, barbs 788 exert a force on the tissue sample in a direction substantially opposite the remainder of the target tissue.

Although FIG. 7C has been described with reference to opposing barbs 788, it should be appreciated that additional barbs may be included on each blade 780 to retain the tissue sample within coring component 750C. Also, it should be appreciated that other retention features may also be used with coring component 750C. For example, as described above with reference to FIG. 7A, coring component 750C may further include a textured surface, an adhesive applied to at least a portion of blade arrangement 784, a needle or a set of opposing jaws positioned within coring component 750C, hooks, spikes, etc. In other embodiments, suction may be provided by a biopsy device having coring component 750C therein so as to retain the tissue sample within the lumen of the coring component.

Furthermore, as noted above, each blade 780 includes cutting edges 785 disposed at the distal end there of blades 780. It should be appreciated that each blade 780 may also include additional cutting edges. For example, each blade may include one or more longitudinally extending cutting edges.

In accordance with embodiments of the present invention illustrated in FIGS. 7A-7C, coring components 750 may be permanently connected to a catheter. In other embodiments, coring components 750 may be removably connected to a catheter.

Figure 8A:
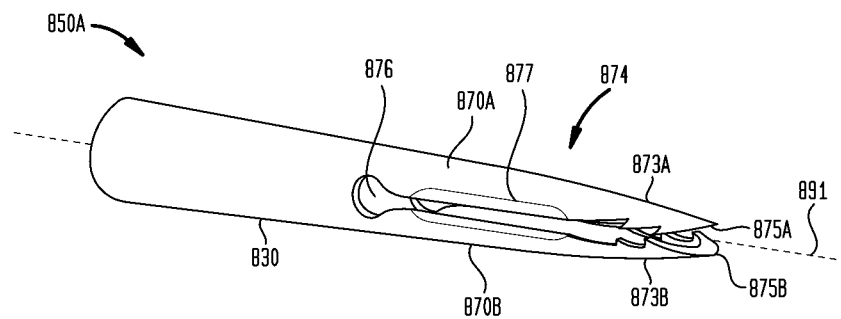
FIG. 8A is a side perspective view of a coring component in accordance with one embodiment of the present invention.
Figure 8B:
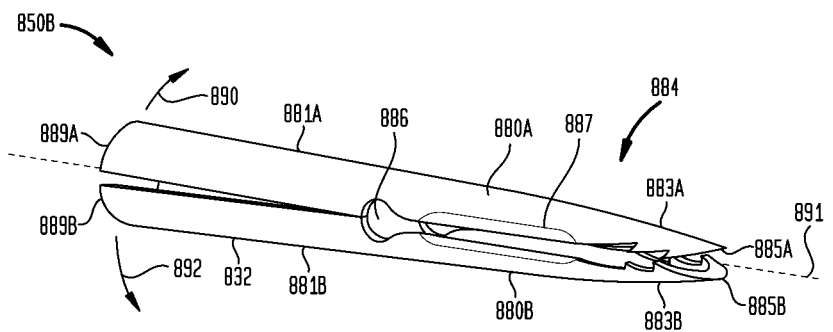
FIG. 8B is a side perspective view of a coring component in accordance with one embodiment of the present invention.

FIGS. 8A and 8B are perspective views of embodiments of coring components 850 in accordance with certain embodiments of the present invention. In particular, FIGS. 8A and 8B illustrate embodiments of coring components 850 configured to sever a tissue sample via closure of elements of coring components 850.

As shown in FIG. 8A, coring component 850A comprises an elongate element 830 having a longitudinal lumen terminating in a distal opening. A distal region of element 830 is formed of a blade arrangement 874 having one or more cutting edges 875 positioned around the distal opening of coring component 850A. In the illustrated embodiment, blade arrangement 874 comprises a pair of opposing blades 870 each having an approximately lunate cross-section. In the embodiments of FIG. 8A, prior to penetration of blades 870 into the target tissue, the distal end of blades 870 are positioned around the distal opening of coring component 850A.

As discussed above with reference to FIG. 7B, blade arrangement 874 is configured to penetrate the target tissue such that a portion of the target tissue having a cross-section defined by an inner diameter of the distal end of blade arrangement 874 is received within the lumen of coring component 850A via the distal opening of coring component 850A. Also, as noted above, blade arrangement 874 is configured to substantially sever the portion of the target tissue received within coring component 850A, referred to as the tissue sample, from the remainder of the target tissue.

In the embodiments illustrated in FIG. 8A, blade arrangement 874 may substantially sever the tissue sample via closure of blades 870. In these embodiments, one or more of blades 870 are configured to flex inwardly towards a longitudinal axis of coring component 850A, shown as axis 891. For example, one or more blades 870 may flex inwards towards a longitudinal axis through the geometric center of coring component 850A. In the specific embodiment of FIG. 8A, both blades 870 flex inwards toward longitudinal axis 891. The inward flexing of blades 870 causes blades 870 to cut through the target tissue positioned there between so as to substantially sever the tissue sample from the remainder of the target tissue.

In particular embodiments illustrated in FIG. 8A, blades 870 are configured to flex inwardly during penetration of the target tissue. In certain such embodiments, blades 870 each comprise a curved or beveled surface 873 (generally and collectively referred to as a "beveled surface" herein). As blades 870 are inserted into the target tissue, the target tissue adjoining beveled surfaces 873 exert a force on the beveled surfaces in the direction of longitudinal axis 891. This force exerted by the target tissue on beveled surfaces 873 increases as blades 870 penetrate deeper into the target tissue.

As the force on bevel surfaces 873 increase, the beveled surfaces are forced inwardly towards axis 891. Each blade has sufficient strength such that as beveled surfaces 873 flex towards axis 891, cutting edges of blades 870 cut through the target tissue. As shown in FIG. 8A, following penetration of blades 870 to a predetermined depth, the distal ends of blades 870 are positioned substantially adjacent axis 891.

In accordance with other embodiments illustrated in FIG. 8A, blades 870 are configured to flex inwards following penetration of the target tissue by blades 870. In one such embodiment, blades 870 comprise a shape memory material configured to flex inwardly toward axis 891 following insertion. Blades 870 may flex inwardly in response to, for example, a change in temperature induced by the target tissue. In another such embodiment, blades 870 may flex inwardly in response to application of an electrical current to blades 870.

The inward flexing of blades 870 causes coring component 850A to obtain a tissue sample that is large enough for proper examination following the procedure. Furthermore, the inward flexing of blades 870 help to ensure that the tissue sample remains within the lumen during removal of the device from the patient.

As explained above, following substantial severing of the tissue sample, the tissue sample is extracted from the target tissue by removing coring component 850A from the target tissue. As described above with reference to FIG. 7A, coring component 850A may be removed from the target tissue in a variety of manners.

As noted above, each blade 870 includes cutting edges 875 disposed at the distal end thereof. It should be appreciated that each blade 870 may also include additional cutting edges. For example, as shown in FIG. 8A, each blade may include one or more longitudinally extending cutting edges, shown as cutting edges 877 in FIG. 8A. Cutting edges 877 and 875 may collectively cut through the target tissue as blades 870 flex inwardly.

In certain embodiments of the present invention, the tissue sample may be substantially severed from the target tissue via a combination of inward flexing of blades 870 and rotation of coring component 850A.

FIG. 8B illustrates an alternative coring component 850B in which a tissue portion received therein, referred to as the tissue sample, may be substantially severed via closure of blades 880 of coring component 850B. As shown in FIG. 8B, coring component 850B comprises an elongate element 832 having a longitudinal lumen terminating in a distal opening. A distal region of elongate element 832 is formed of a blade arrangement 884 having one or more cutting edges 885 positioned around the distal opening of coring component 850A. In the illustrated embodiment, blade arrangement 884 comprises a pair of opposing blades each having an approximate lunate cross-section.

As discussed above with reference to FIG. 7B, blade arrangement 884 is configured to penetrate the target tissue such that a portion of the target tissue having a cross-section defined by the distal end of blade arrangement 884 is received within the lumen of coring component 850B via the distal opening. Also, as noted above, blade arrangement 884 is configured to substantially sever the portion of the target tissue received within coring component 850B, referred to as the tissue sample, from the remainder of the target tissue.

In the embodiments illustrated in FIG. 8B, blade arrangement 884 may substantially sever the tissue sample via closure of blades 880. In these embodiments, one or more of blades 880 are configured to flex inwardly towards a longitudinal axis of coring component 850B, shown as axis 891. The inward flexing of blades 880 causes the blades to cut through the target tissue positioned there between so as to substantially sever the tissue sample from the remainder of the target tissue.

In particular embodiments illustrated in FIG. 8B, blades 880 are configured to flex inwardly during penetration of the target tissue. In certain such embodiments, blades 880 each comprise a beveled surface 883. As blades 880 are inserted into the target tissue, the target tissue adjoining beveled surfaces 883 exert a force on the beveled surfaces in the direction of axis 891. This force exerted by the target tissue on beveled surfaces 883 increases as blades 880 penetrate deeper into the target tissue.

As the force on bevel surfaces 883 increase, beveled surfaces 883 flex inwardly towards longitudinal axis 891. Each blade has sufficient strength such that as beveled surfaces 883 flex towards axis 891, cutting edges of blades 880 cut through the target tissue. As shown in FIG. 8B, following penetration of blades 880 to a predetermined depth, the distal ends of blades 880 are positioned substantially adjacent axis 891.

In accordance with other embodiments illustrated in FIG. 8B, blades 880 are configured to flex inwards following penetration of the target tissue by blades. In these embodiments, blades 880 comprise a shape memory material configured to flex inwardly toward axis 891 following insertion. In one such embodiment, following penetration, blades 880 flex inwardly in response to a change in temperature induced by the target tissue. In another such embodiment, blades 880 may flex inwards in response to application of an electrical current to blades 880.

As shown in FIG. 8B, in certain embodiments coring component 850B comprises a two-piece component comprising opposing elements 881. Opposing elements 881 collectively define the longitudinal lumen extending there through. In the embodiments of FIG. 8B, elements 881 are connected to one another via a hinge arrangement 889. In certain embodiments, hinge arrangement 889 enhances the ability of blades 880 to flex inwards in response to forces on beveled surfaces 883 during penetration. In other embodiments, hinge arrangement 889 enhances the response of blades comprising shape memory materials to changes in temperature or to an electrical current.

In other embodiments, hinge arrangement 889 provides a surgeon with the ability to mechanically close blades 880. In certain embodiments, a biopsy device having coring component 850B therein includes a component which permits a surgeon to actuate hinge arrangement 889. Actuation of hinge arrangement 889 causes the distal ends of one or more of blades 880 to flex inwards towards axis 891. In such embodiments, the proximal ends 889 of elements 881 are forced away from axis 891, shown by directional arrows 890, 892. In embodiments of the present invention, the surgeon may actuate hinge mechanism during or following penetration of the target tissue by blades 880.

In certain embodiments of the present invention, the tissue sample may be substantially severed from the target tissue via a combination of inward flexing of blades 880 and rotation of coring component 850B.

In the above embodiments, the inward flexing of blades 880 causes coring component 850B to obtain a tissue sample that is large enough for proper examination following the procedure. Furthermore, the inward flexing of blades 880 help to ensure that the tissue sample remains within the lumen during removal of the device from the patient.

As explained above, following the substantially severing of the portion of the target tissue received within coring component 850B, the tissue portion is extracted from the target tissue by removing coring component 850B from the target tissue. As described above with reference to FIG. 7A, coring component 850B may be removed from the target tissue in a variety of manners.

Figure 9:
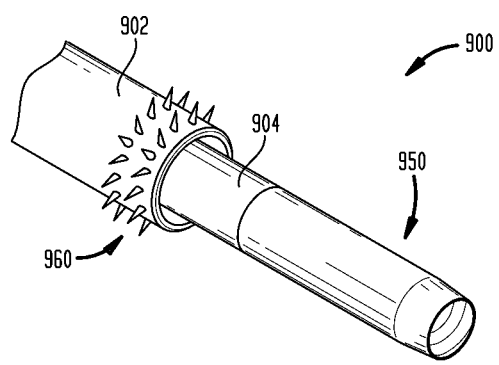
FIG. 9 is a front perspective view of a biopsy device having an anchoring element in accordance with embodiments of the present invention.

As noted above with reference to FIGS. 3A and 3B, an endoscopic biopsy device in accordance with embodiments of the present invention may be anchored or secured to a target tissue prior to sampling of the target tissue. FIG. 9 illustrates a distal portion of embodiments of an endoscopic biopsy device 900 including an anchoring element 960.

As noted above, an endoscopic biopsy device in accordance with embodiments of the present invention, such as biopsy device 900, includes a sheath 902, a catheter 904 and a sampling component 950 positioned at the distal end of catheter 904. In the illustrated embodiment, sampling component 950 comprises a coring component 950.

As shown below, anchoring element 960 causes biopsy device 900 to be located at the proper location prior to insertion of the coring component 950 into the target tissue. Furthermore, anchoring element 960 prevents coring component 950 from slip, sliding or moving relative to the target tissue immediately before or during penetration.

In the embodiment of FIG. 9, during insertion of biopsy device 900 into the patient, coring component 950 is positioned within sheath 902. Biopsy device 900 is inserted into the patient until a distal end of sheath 902 is positioned in contact with a target tissue. While in contact with the target tissue, anchoring element 960 secures biopsy device 900 with respect to the target tissue.

As shown in FIG. 9, anchoring element 960 comprises a plurality of spikes 960 positioned on the distal end of sheath 902. When sheath 902 is placed in contact with the target tissue, spikes 960 attach or secure sheath 902 to the target tissue. Spikes 960 are configured to remain attached to the target tissue at least until coring component 950 penetrates the target tissue. Spikes 960 are further configured to be detached from the target tissue with minimal damage to the target tissue.

In certain embodiments, spikes 960 are fixed spikes positioned permanently at the distal end of sheath 902. In other embodiments, spikes 960 comprise retractable spikes configured to be extended from, and withdrawn into, sheath 902.

Although FIG. 9 has been discussed herein with reference to spikes 960, it should be appreciated that anchoring element 960 may further comprise a variety of additional embodiments. For example, in certain embodiments, anchoring element 960 may comprise a textured surface positioned at the distal end of sheath 902. In these embodiments, the surface of the distal end of sheath 902 may be modified so that sheath 902 will adhere to the target tissue. This may include one or more rough portions, barbs etc.

In other embodiments, anchoring element 960 may comprise an adhesive applied to the distal end of sheath 902. For example, in such embodiments a reusable adhesive, such as a Gecko-Mussel adhesive may be used.

Furthermore, although FIG. 9 has been discussed with reference to an anchoring element 960 positioned at the distal end of sheath 902, it should also be appreciated that coring component 950 may have an anchoring element 960 positioned thereon. In these embodiments, sheath 902 would be positioned adjacent the target tissue and coring component 950 would be at extended to the target tissue. Prior to penetration of the target tissue by coring component 950, anchoring element 960 on coring component 950 would engage the target tissue. In such embodiments, anchoring element 960 retains coring component 950 in position with respect to the target tissue during initial penetration. Anchoring element 960 of such embodiments may include any of the anchoring elements discussed above, including rough surface portions, spikes, barbs, adhesive, etc. In certain such embodiments, the one or more blades of coring component 950 may act alone to anchor coring component 950 to the target tissue prior to penetration.

Figure 10A:
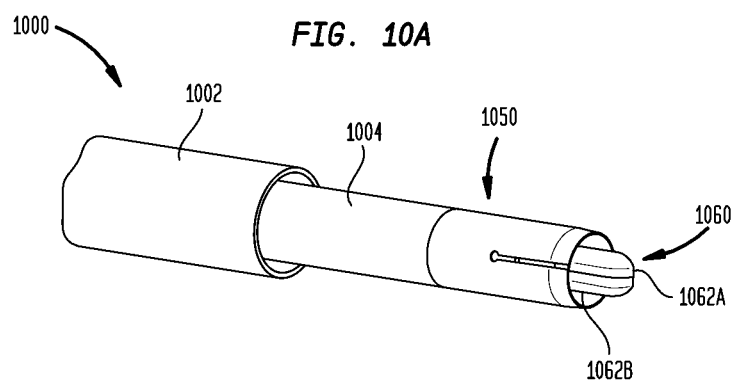
FIG. 10A is a front perspective view of a biopsy device having an anchoring element in accordance with one embodiment of the present invention.
Figure 10B:
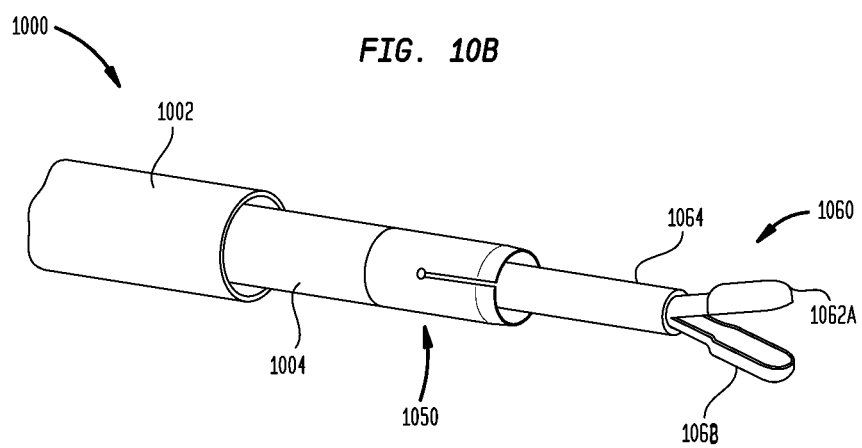
FIG. 10B is a front perspective view of the embodiment of a biopsy device shown in FIG. 10A.

As noted above with reference to FIG. 3B, certain embodiments of the present invention may include an element configured to be controllably extended from the biopsy device to secure the biopsy device to the target tissue, referred to as an extendible anchoring element. FIGS. 10A and 10B are front perspective views of a distal region of an endoscopic biopsy device 1000 having such an extendible anchoring element, referred to as anchoring element 1060.

Similar to embodiments described above, biopsy device 1000 comprises a sheath 1002 having a lumen there through. Extending through the lumen is a catheter 1004 having a sampling component 1050 positioned at the distal end thereof. In the embodiments of FIGS. 10A and 10B, sampling component 1050 comprises a coring component 1050.

FIG. 10A illustrates the configuration of biopsy device 1000 prior to extension of anchoring element 1060. FIG. 10B illustrates the configuration of biopsy device 1000 following extension of anchoring element 1060, but prior to extension of coring component 1050 to the target tissue.

As shown in FIG. 10A, in a first configuration anchoring element 1060 is positioned within coring component 1050. As noted above, in embodiments of the present invention, catheter 104 and coring component 1050 have a lumen extending therein. As shown in FIGS. 10A and 10B, anchoring element 1060 may be positioned in this lumen.

Anchoring element 1060 comprises an elongate shaft 1064 and a pair of opposing jaws 1062. In these embodiments, a surgeon may extend anchoring element 1060 from with the lumen of coring component 1050 such that jaws 1062 contact the target tissue. Jaws 1062 may then be closed around a portion of the target tissue to secure biopsy device 1000 to the target tissue. In embodiments illustrated in FIGS. 10A and 10B, jaws 1062 close around a portion of the target tissue such that coring component 1050 may penetrate the target tissue around closed jaws 1062.

In certain embodiments of the present invention, jaws 1062 may release the target tissue during penetration of the target tissue by coring component 1050. In other embodiments of the present invention, jaws 1062 may remain attached to the target tissue during and following penetration of the component. As such, as described above with reference to FIGS. 6-7C, coring component 1050 is configured to substantially sever at least the portion of the target attached to jaws 1062. In these embodiments, because jaws 1062 remain attached to the severed tissue portion, jaws 1062 function as a retention feature to assist in the removal of the severed portion from the target tissue.

Although FIGS. 10A and 10B have been described herein with reference to a sampling component 1050 in the form of a coring component, it should would be appreciated that anchoring element 1060 comprising jaws 1062 may be used in conjunction with alternative sampling components. For example, in alternative embodiments of the present invention, a sampling component in the form of a jaws arrangement, such as the jaws arrangement described with reference to FIG. 5, may be used in conjunction with anchoring element 1060. In certain such embodiments, the anchoring element 1060 would be controllable extended from within the opposing jaws of the jaws arrangement.

Furthermore, although anchoring element 1060 has been shown extending from within coring component 1050, it should be appreciated that anchoring may be extended from other locations as well, such as adjacent the coring component, around the coring component, etc.

Figure 11A:
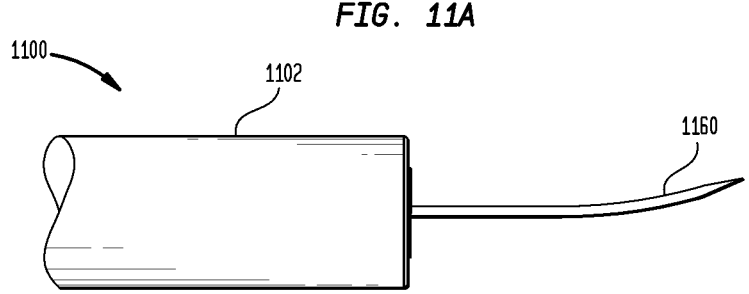
FIG. 11A is a perspective view of a biopsy device having an anchoring element in accordance with one embodiment of the present invention.
Figure 11B:
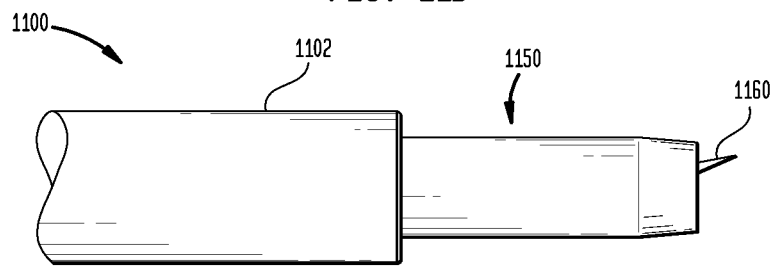
FIG. 11B is a perspective view of the embodiment of a biopsy device shown in FIG. 11A.

FIGS. 11A and 11B are front perspective views of a distal region of embodiments of an endoscopic biopsy device 1100 having an extendible anchoring element, referred to as anchoring element 1160.

Similar to embodiments described above, biopsy device 1100 comprises a sheath 1102 having a lumen there through. Extending through the lumen is a catheter (not shown) having a sampling component 1150 positioned at the distal end thereof. In the embodiments of FIGS. 11A and 11B, sampling component 1150 comprises a coring component 1150.

FIG. 11A illustrates the configuration of biopsy device 1100 following extension of anchoring element 1160, but prior to extension of coring component 1150. FIG. 11B illustrates the configuration of biopsy device 1100 following extension anchoring element 1160 and of coring component 1150. As shown, anchoring element 1160 comprises a needle like component, referred to as needle 1160. In these embodiments, a surgeon may extend needle 1160 from within coring component 1150 such that needle 1160 penetrates a portion of the target tissue and remains secured therein. In embodiments of the present invention, coring component 1150 penetrates the target tissue around needle 1160.

In certain embodiments of the present invention, needle 1160 may be removed from the target tissue during penetration of the target tissue by coring component 1150. In other embodiments of the present invention, needle 1160 may remain attached to the target tissue during and following penetration of the component. In such embodiments, coring component 1150 penetrates the target tissue around needle 1160. As such, as described above with reference to FIGS. 6-7C, coring component 1150 is configured to substantially sever at least the portion of the target tissue attached to needle 1160. In these embodiments, because needle 1160 remains attached to the severed tissue portion, needle 1160 functions as a retention feature to assist in the removal of the severed portion from the target tissue.

In the embodiments illustrated in FIGS. 11A and 11B, the distal end of needle 1160 is curved. However, it should be appreciated that other configurations for needle 1160 are within the scope of the present invention. For example, in certain embodiments, needle 1160 may be straight.

Furthermore, FIGS. 11A and 11B illustrate the use of a single needle. However, it should also be appreciated that multiple extendible needles may also be used in substantially the same manner as described above. It should also be appreciated that in embodiments of the present invention, needle 1160 may be net or straight, solid or hollow wire, and may be integrated or separate from any of sheath 1102, coring component 1150 or any other utilized device.

Although FIGS. 11A and 11B have been described herein with reference to a sampling component 1150 in the form of a coring component, it should be appreciated that anchoring element 1160 may be used in conjunction with alternative sampling components. For example, in alternative embodiments of the present invention, a sampling component in the form of a jaws arrangement, such as the jaws arrangement described with reference to FIG. 5, may also be used.

As shown in FIGS. 11A and 11B, anchoring element 1160 extends from within coring component 1150. However, it should be appreciated that in other embodiments, anchoring element 1160 may extend from other locations as well, such as adjacent to coring component 1150.

Figure 12A:
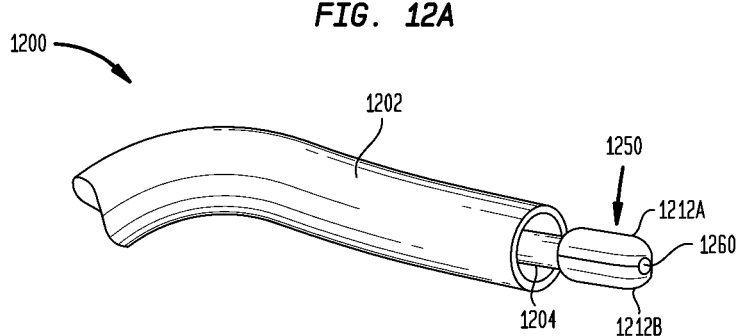
FIG. 12A is a front perspective view of a biopsy device having an anchoring element in accordance with one embodiment of the present invention.
Figure 12B:
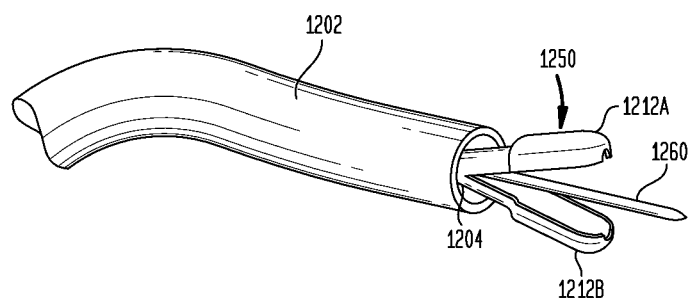
FIG. 12B is a perspective view of the embodiment of a biopsy device shown in FIG. 12A.

FIGS. 12A and 12B illustrate the distal region of an endoscopic biopsy device 1200 in accordance with embodiments of the present invention. As show, biopsy device 1200 is similar to the embodiments described above with reference to FIG. 5 and includes a sheath 1202, and a jaws arrangement 1250. Jaws arrangement 1250 includes a shaft 504 and opposing jaws 512.

FIG. 12A illustrates the configuration of biopsy device 1200 prior to extension of anchoring element 1260 to the target tissue. FIG. 12B illustrates the configuration of biopsy device 1200 following extension of anchoring element 1260, but prior to extension of jaws arrangement 1250 to the target tissue.

As shown, anchoring element 1260 comprises a needle like component, referred to as needle 1260. In these embodiments, a surgeon may extend needle 1260 from within jaws arrangement 1250 such that needle 1260 penetrates a portion of the target tissue and remains secured therein. In embodiments of the present invention, jaws arrangement 1250 samples the portion of the target tissue around needle 1260. More specifically, in the embodiments of FIGS. 12A and 12B, jaws 512 are positioned around the portion of the target tissue attached to needle 1260. As explained above, closure of jaws 512 substantially sever at least the portion of the target tissue attached to needle 1260 from the remainder of the target tissue.

In accordance with certain embodiments shown in FIGS. 12A and 12B, needle 1260 may be extended from jaws arrangement 1250 through an aperture 1262 in jaws 1212. In these embodiments, needle 1260 may be extended to the target tissue without opening jaws 1212. Furthermore, in such embodiments, needle 1260 may be inserted into the target tissue beyond jaws 1212 without interfering with the closure of jaws 1212.

As shown, FIGS. 12A and 12B illustrate the use of a single needle. However, it should also be appreciated that multiple extendible needles may be used in substantially the same manner as described above. It should also be appreciated that in embodiments of the present invention, needle 1260 may be net or straight, solid or hollow wire, and may be integrated or separate from any of sheath 1202, coring component 1250 or any other utilized device.

Figure 13A:
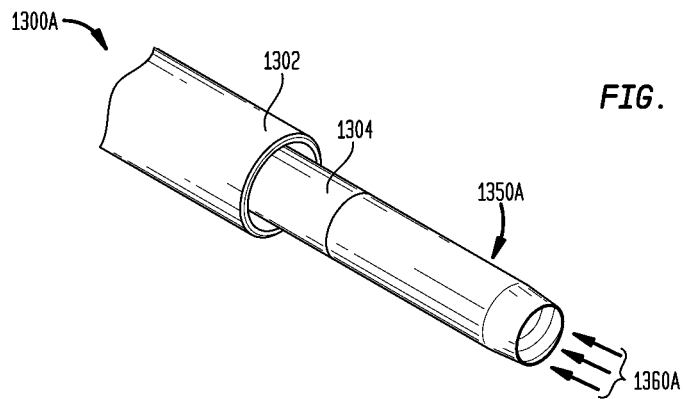
FIG. 13A is a front perspective view of a biopsy device having an anchoring element in accordance with one embodiment of the present invention.

FIG. 13A illustrates a distal region of an endoscopic biopsy device 1300A in which suction is provided via a biopsy port of the device to secure the biopsy device to the target tissue and or to secure a tissue sample within a coring component. In the embodiments illustrated in FIG. 13A, biopsy device 1300A comprises a sheath 1302 and a coring component 1350A. Extending through a lumen of sheath 1302 is a catheter 1304 having coring component 1350A disposed at the distal end thereof. Coring component 1350A comprises an element having a longitudinal lumen terminating in a distal opening 1306. In the embodiments of FIG. 13A, a lumen of catheter 1304 is operationally contiguous with the lumen of coring component 1350A. As described above with reference to FIG. 6, opening 1306 is configured to receive a portion of the target tissue therein, referred to herein as a tissue sample.

As shown by arrows 1360A, suction is provided via opening 1306. In these embodiments, as coring component 1350A is extended to the target tissue, the suction through opening 1306 causes coring component 1350A to be secured to the target tissue.

In certain embodiments, the suction through opening 1306 may be controlled by the surgeon. For example, in certain embodiments the surgeon may control the magnitude of the suction. In other embodiments, the surgeon may disable the suction during or following penetration of coring component 1350A.

In other embodiments of the present invention, the suction continues during penetration of the component. In these embodiments, the suction functions as a retention feature to assist in the removal of the tissue sample from the target tissue.

Figure 13B:
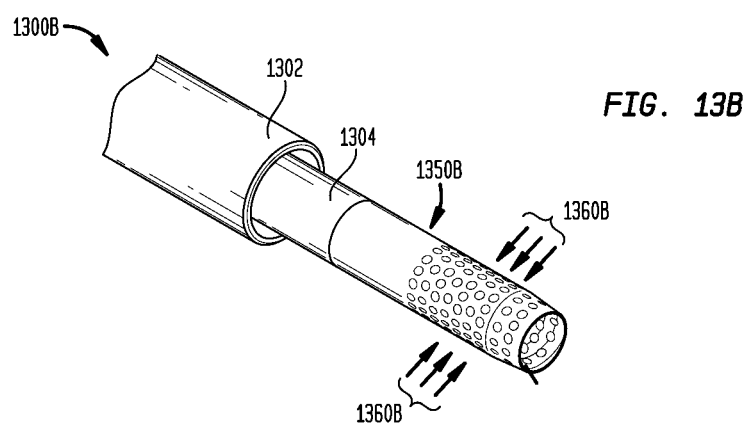
FIG. 13B is a front perspective view of a biopsy device having an anchoring element in accordance with one embodiment of the present invention.

FIG. 13B illustrates another embodiment of the present invention in which suction is provided via one or more openings in a coring component 1350B of a endoscopic biopsy device 1300B to secure the biopsy device to the target tissue. In the embodiments illustrated in FIG. 13B, biopsy device 1300B comprises a sheath 1302 and a coring component 1350B. Extending through a lumen of sheath 1302 is a catheter 1304 having coring component 1350B positioned at the distal end thereof. In the embodiments of FIG. 13B, catheter 1304 and coring component 1350 have a lumen extending longitudinally there through. The lumen terminates in an opening 1306.

In the embodiments illustrated in FIG. 13B, coring component 1350 comprises a plurality of openings 1310 therein. Openings 1310 are substantially perpendicular to a longitudinal axis through the geometric center of opening 1306. As shown by arrows 1360B, suction is provided via openings 1310. In these embodiments, as coring component 1350B is extended to the target tissue, the suction through openings 1310 causes coring component 1350B to be secured to the target tissue.

In certain embodiments, the suction through openings 1310 may be controlled by the surgeon. For example, in certain embodiments the surgeon may control the magnitude of the suction. In other embodiments, the surgeon may disable the suction during or following penetration of coring component 1350B.

In other embodiments of the present invention, the suction continues during penetration of the component. In these embodiments, the suction functions as a retention feature to assist in the removal of the tissue sample from the target tissue.

Figure 13C:
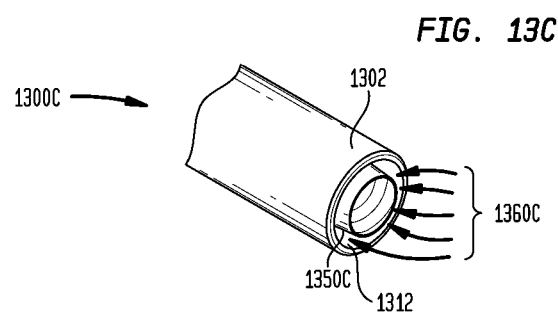
FIG. 13C is a front perspective view of a biopsy device having an anchoring element in accordance with one embodiment of the present invention.

FIG. 13C illustrates still other embodiments of the present invention in which suction is provided via an endoscopic biopsy device 1300C to secure the biopsy device to the target tissue. In the embodiments illustrated in FIG. 13C, biopsy device 1300C comprises a sheath 1302 and a coring component 1350C. Extending through a lumen 1312 of sheath 1302 is a catheter 1304 having coring component 1350C positioned at the distal end thereof. In the embodiments of FIG. 13C, catheter 1304 and coring component 1350C have a lumen extending longitudinally there through. The lumen terminates in an opening 1306.

As shown by arrows 1360C, in the illustrated embodiment, suction is provided around coring component 1350C via lumen 1312. In these embodiments, as coring component 1350C is extended to the target tissue, the suction through lumen 1312 around coring component 1350C causes biopsy device 1300C to be secured to the target tissue.

In certain embodiments, the suction through lumen 1312 may be controlled by the surgeon. For example, in certain embodiments the surgeon may control the magnitude of the suction. In other embodiments, the surgeon may disable the suction during or following penetration of coring component 1350C. In other embodiments of the present invention, the suction continues during penetration of the component.

Although FIGS. 13A-13C have been discussed reference to coring components 1350, it should be appreciated that in alternative embodiments other sampling components may also be used. For example, in particular embodiments, a jaws arrangement, such as the jaws arrangement described above with reference to FIG. 5 may be used.

In one such embodiment in which a jaws arrangement may be used in conjunction with suction, an internal lumen may be included within the jaws arrangement to provide suction at the target tissue between the opposing jaws of the jaws arrangement. In another embodiment, suction may be provided around the jaws via a lumen of a sheath.

An endoscopic biopsy device in accordance with embodiments of the present invention may be further configured to deliver a treatment to the target tissue prior to, during, or after sampling of the target tissue. The treatment delivered to the target tissue may take a variety of forms.

In certain embodiments of the present invention, the biopsy device may be configured for hemostasis. For example, in one such embodiment, the biopsy device may be configured to cauterize the tissue at or near the sample during or after the sampling with the sampling component. In alternative embodiments, the biopsy device may be configured to apply a hemostasis coating at or near the sample site to reduce the loss of blood. This coating may be applied in a variety of ways including by applying an agent to the biopsy sampling component prior to the sampling process, or by spraying, injecting, misting or swabbing an agent onto the tissue. As such, a variety of coating mechanisms may be incorporated into the biopsy device.

In other embodiments of the present invention, biopsy device may be further configured to deliver a therapeutic agent, marker or other material to the target tissue. As described above with reference to FIGS. 5 and 6, the catheter and sampling component may have a lumen extending there through. As such, the therapeutic agent, marker, diagnostic agent or other material may be delivered via the lumen extending through catheter and sampling component. These treatments may include, for example, antiseptic, anesthesia, antibacterial or cleaning agents, rinse solutions, genetic or other material in a solid, liquid, solution, gel, vapor, gas or any other form.

In still other embodiments, the biopsy device may be further configured to be to suture the sample site following sampling. This suturing may be done by the coring component, or by one or more components extending from in or near the coring component. As noted above with reference to FIGS. 5 and 6, the catheter and sampling component may have a lumen extending there through. As such, an additional component for suturing the target tissue may be inserted through this lumen.

As noted above, such treatments may be delivered through the contiguous lumens of the catheter and the sampling components. In other embodiments, an additional lumen may be provided through the catheter and sampling component so as to provide an alternate channel for delivery of treatments or which may otherwise be utilized by a surgeon.

Furthermore, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A device for sampling target tissue within a patient, comprising:
   a coring component having:
      a longitudinal lumen terminating in a distal opening; and
      a distal region formed of one or more distally extending flexible blades each having a distal end positioned around said distal opening,
      wherein the blades are configured to move toward each other when the coring component is penetrating into the target tissue along a longitudinal axis of the coring component;
      wherein said blades are configured via the movement toward each other to substantially sever a tissue sample from the target tissue during penetration.

2. The device of claim 1, wherein said one or more blades are configured to penetrate
   the target tissue such that a tissue sample having a cross-section defined by said distal ends of said one or more blades is received within said lumen of said coring component via said distal opening.

3. The device of claim 2, wherein each said blade has an approximate lunate cross-section along a lateral axis substantially parallel to said distal opening.

4. The device of claim 2, wherein said coring component comprises two or more elongate blades, at least one of said blades configured to flex inwardly towards a longitudinal axis of said coring component in response to penetration of the target tissue by said blades.

5. The device of claim 4, wherein a distal region of at least one of said blades opposing said lumen of said coring component comprises a beveled surface.

6. The device of claim 2, wherein said coring component comprises two or more elongate blades, each of said blades configured to flex inwardly towards a longitudinal axis of said coring component following penetration of the target tissue by said blades.

7. The device of claim 6, wherein at least one of said blades comprise a shape memory material responsive to a change in temperature that occurs following said penetration.

8. The device of claim 6, wherein at least one of said blades comprise a shape memory material responsive to an applied electrical current.

9. The device of claim 4, wherein said coring component comprises two or more separate elements defining said lumen, and wherein said elements are connected by a hinge arrangement.

10. The device of claim 9, wherein said hinge arrangement may be actuated so as to cause at least one of said blades to flex inwardly towards said longitudinal axis.

11. The device of claim 2, wherein said device further comprises an elongate catheter having proximal and distal ends and a lumen longitudinally extending there through, wherein said coring component is disposed at said distal end of said catheter, and wherein said lumen of said catheter that is operationally contiguous with said lumen of said coring component.

12. The device of claim 2, further comprising:
   an anchoring element configured to secure the device to the target tissue.

13. The device of claim 12, wherein said anchoring element comprises an element disposed on a distal end of at least one of said one or more blades.

14. The device of claim 12, wherein said anchoring element is configured to be controllably extended from within said coring component to secure the device to the target tissue.

15. The device of claim 12, wherein said anchoring element is configured to be controllably extended around said coring component to secure the device to the target tissue.

16. The device of claim 14, wherein said anchoring element comprises an extendible needle.

17. The device of claim 12, wherein said anchoring element comprises an extendible needle.

18. The device of claim 11, wherein said anchoring element comprises a suction system configured to secure said catheter.

19. The device of claim 2, wherein said coring component further comprises at least one tissue retention feature configured to secure said tissue sample within said lumen of said coring component.

20. The device of claim 19, wherein said at least one tissue retention feature comprises:
a textured surface of a portion of at least one of said one or more blades adjacent said lumen of said coring component.

21. The device of claim 19, wherein said at least one tissue retention feature comprises:
an adhesive having an adhesion force that may be overcome with sufficient manual force.

22. The device of claim 19, wherein said at least one tissue retention feature comprises:
a barb disposed on at least one of said one or more blades adjacent said lumen of said coring component.

23. The device of claim 19, wherein said device further comprises an elongate catheter having proximal and distal ends and a lumen longitudinally extending there through, wherein said coring component is disposed at said distal end of said catheter, and wherein said at least one tissue retention feature comprises a suction system configured to provide suction via said catheter.

24. The device of claim 23, wherein said suction is provided through said coring component.

25. The device of claim 23, wherein said suction is provided around said coring component.

26. The device of claim 25, wherein a distal region of said sheath has a fixed radius of curvature.

27. The device of claim 2, wherein said blades are configured to anchor the device to the target tissue.

28. The device of claim 2, further comprising an endoscopic device having:
an elongate catheter having proximal and distal ends and a lumen longitudinally extending there through, wherein said coring component is disposed at said distal end of said catheter; and
a sheath configured to be inserted into the patient and configured to have said catheter inserted therein.

29. The device of claim 28, wherein a distal region of said sheath has a fixed radius of curvature.

30. The device of claim 29, further comprising:
one or more components configured to controllably curve a distal region of said sheath.

31. The device of claim 2, further configured to deliver a treatment to the target tissue.

32. The device of claim 31, wherein said treatment comprises hemostasis of the target tissue.

33. The device of claim 32, wherein said coring component is configured to cauterize the target tissue.

34. The device of claim 32, wherein said coring component is configured to apply a hemostasis coating to the target tissue.

35. The device of claim 31, wherein said treatment comprises delivery of a therapeutic agent to the target tissue.

36. A device For sampling target tissue within a patient comprising:
a coring component having:
a longitudinal lumen terminating in a distal opening: and
a distal region formed of one or more distally extending flexible blades each having a distal end positioned around said distal opening,
wherein said blades are configured to penetrate the target tissue such that a tissue sample having a cross-section defined by said distal ends of said blades is received within said lumen of said coring component via said distal opening, and
wherein said blades are configured to substantially sever said tissue sample from the target tissue, and
wherein said coring component further comprises two or more elongate blades, each of which is configured to flex inwardly towards a longitudinal axis of said coring component toward each other when penetrating said target tissue by said blades, and
wherein said coring component further comprises at least one tissue retention feature configured to secure said tissue sample within said lumen of said coring component.

37. A device for sampling target tissue within a patient, comprising:
a coring component having:
a longitudinal lumen terminating in a distal opening;
a distal region formed of distally extending flexible blades each having a distal end positioned around said distal opening, wherein the blades are configured to move toward each other when the distal region is penetrating into the target tissue along a longitudinal axis of the coring component;
wherein said blades are configured to substantially sever said tissue sample from the target tissue via movement of the blades toward each other during penetration into the target tissue; and
an elongate catheter having proximal and distal ends and a lumen longitudinally extending there through, wherein said coring component is disposed at said distal end of said catheter, and wherein said lumen is operationally contiguous with said lumen of said coring component.

* * * * *